United States Patent [19]

Wasley et al.

[11] Patent Number: 4,758,559
[45] Date of Patent: Jul. 19, 1988

[54] PYRROLO[1,2-A] [4,1]BENZOXAZEPINE DERIVATIVES USEFUL AS CALMODULIN AND HISTAMINE INHIBITORS

[75] Inventors: Jan W. F. Wasley, Chatham; Jon Norman, Mountainside, both of N.J.

[73] Assignee: Ciba-Geigy Corporation, Ardsley, N.Y.

[21] Appl. No.: 821,110

[22] Filed: Jan. 21, 1986

[51] Int. Cl.$^4$ .................. A61K 31/55; C07D 413/06; C07D 413/14; C07D 498/04
[52] U.S. Cl. .................................. 514/211; 540/543; 540/547
[58] Field of Search .................. 540/547, 543; 514/211

[56] References Cited

U.S. PATENT DOCUMENTS

| | | | |
|---|---|---|---|
| 4,029,672 | 1/1977 | Effland et al. | 540/547 X |
| 4,045,448 | 8/1977 | Effland et al. | 260/326.5 B |
| 4,053,599 | 4/1977 | Effland et al. | 424/250 |
| 4,169,095 | 6/1979 | Effland et al. | 260/326.5 B |
| 4,608,374 | 8/1986 | Effland et al. | 540/547 X |

OTHER PUBLICATIONS

Cheeseman et al, J. Het. Chem., vol. 22 (1985), pp. 809–811.
Massa et al, Farmaco, Ed. Sci. 1983, vol. 38, pp. 893–903.
Msan, 1987–Loperamide Hydrochloride.
Goodman and Gilman's –The Pharmacological Basis of Therapeutics, 7th Edition 1985, p. 517.
Massa et al., Chem. Abstract, 100, 44890c (1984).
Massa et al., J. Het. Chem. 18, 829 (1981).

Primary Examiner—Donald G. Daus
Assistant Examiner—William A. Teoli, Jr.
Attorney, Agent, or Firm—Norbert Gruenfeld

[57] ABSTRACT

Disclosed are the compounds of the formula

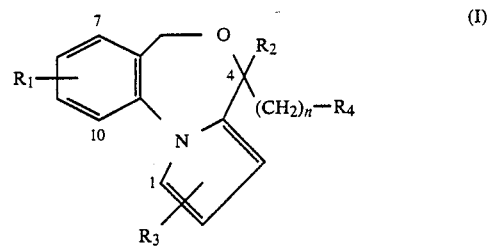

wherein n represents the integer 1,2,3 or 4; $R_1$ represents hydrogen, lower alkyl, halogen, trifluoromethyl, hydroxy or lower alkoxy; $R_2$ represents hydrogen or lower alkyl; $R_3$ represents hydrogen, lower alkyl or halogen; $R_4$ represents amino, lower alkylamino, di-lower alkylamino, morpholino, N-lower alkyl or N-aryl piperazino, pyrrolidino, piperidino or substituted piperidino selected from

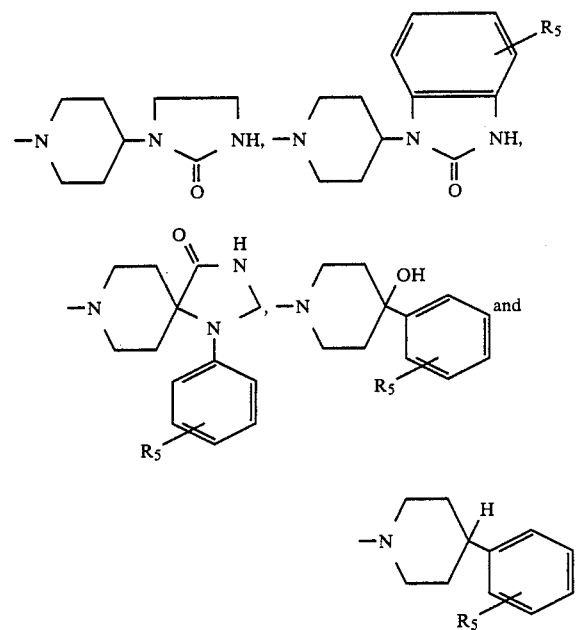

in which $R_5$ represents hydrogen, halogen or lower alkyl; and pharmaceutically acceptable salts thereof; which are useful in mammals as calmodulin antagonists for the treatments of gastrointestinal disorders.

15 Claims, No Drawings

PYRROLO[1,2-A] [4,1]BENZOXAZEPINE DERIVATIVES USEFUL AS CALMODULIN AND HISTAMINE INHIBITORS

SUMMARY OF THE INVENTION

The present invention is directed to 4-substituted-4H,6H-pyrrolo[1,2-a][4,1]benzoxazepines which are useful as selective calmodulin antagonists demonstrating gastrointestinal antisecretory activity, e.g. antidiarrheal and antiulcer activity. The compounds of the inventon also possess histamine inhibitory and acid secretion inhibitory properties.

The foregoing attributes render the compounds of this invention particularly useful when administered, alone or in combination, to mammals for the treatment of gastrointestinal disorders, e.g. diarrhea, ulcers of the gastrointestinal system, gastric acidity, inflammatory bowel disease and dehydration.

DETAILED DISCLOSURE OF THE INVENTION

This invention relates to the novel 4H,6H-pyrrolo[1,2-a][4,1]benzoxazepine derivatives of formula I, processes for preparing the same, pharmaceutical compositions comprising said compounds and methods of treating gastrointestinal disorders by administration of said compounds and pharmaceutical compositions to mammals.

Particularly the invention relates to compounds of the formula I

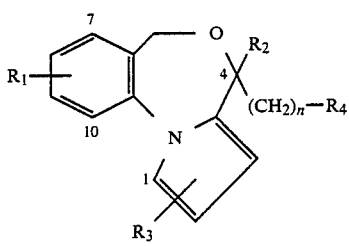

wherein n represents the integer 1, 2, 3 or 4; $R_1$ represents hydrogen, lower alkyl, halogen, trifluoromethyl, hydroxy or lower alkoxy; $R_2$ represents hydrogen or lower alkyl; $R_3$ represents hydrogen, lower alkyl or halogen; $R_4$ represents amino, lower alkylamino, di-lower alkylamino, morpholino, N-lower alkyl or N-aryl-piperazino, pyrrolidino, piperidino or substituted piperidino selected from

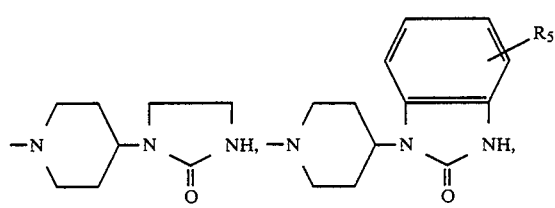

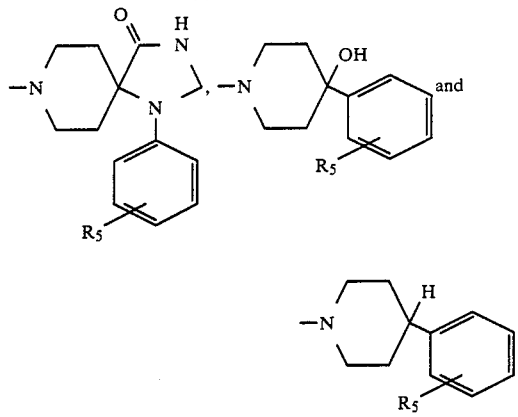

in which $R_5$ represents hydrogen, halogen or lower alkyl; and pharmaceutically acceptable salts thereof.

Preferred are said compounds of formula I wherein n represents 1 or 2; $R_4$ represents substituted piperidino as defined above; and pharmaceutically acceptable salts thereof.

Of particular interest are the compounds of formula

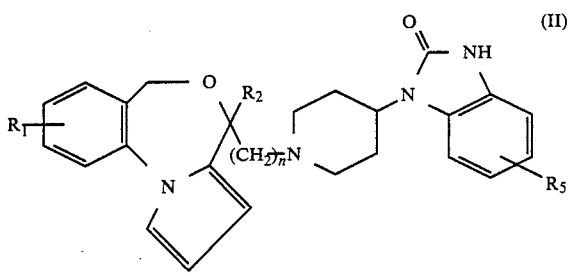

wherein $R_1$ represents hydrogen, lower alkyl, halogen, trifluoromethyl, hydroxy or lower alkoxy; $R_2$ represents hydrogen or lower alkyl; n represents an integer from 1 to 4; and $R_5$ represents hydrogen, halogen or lower alkyl; and pharmaceutically acceptable salts thereof.

Further preferred are said compounds of formula II wherein n represents the integer 1 or 2; $R_2$ represents straight chain lower alkyl of 1 to 4 carbon atoms; $R_1$ and $R_5$ represent hydrogen or halogen; and pharmaceutically acceptable salts thereof.

Particularly preferred is the compound of formula II wherein $R_1$ and $R_5$ represents hydrogen, $R_2$ represents methyl or ethyl; and n represents the integer 1; and pharmaceutically acceptable salts thereof.

The general definitions used herein have the following meaning within the scope of the present invention.

Halogen is preferably chloro and fluoro but may also be bromo or iodo.

The term "lower" referred to above and hereinafter in connection with organic radicals or compounds respectively defines such with up to and including 7, preferably up to and including 4 and advantageously one or two carbon atoms.

Lower alkyl contains 1 to 7 carbon atoms, preferably 1 to 4 carbon atoms, is advantageously straight chain and represents for example methyl, ethyl, propyl or butyl, advantageously methyl.

Lower alkoxy is preferably straight chain alkoxy containing 1 to 4 carbon atoms and represents for example methoxy, ethoxy, propoxy, advantageously methoxy.

Aryl represents preferably phenyl or phenyl monosubstituted by lower alkyl or halogen.

Pharmaceutically acceptable salts are acid addition salts, which are preferably such of therapeutically acceptable inorganic or organic acids, such as strong mineral acids, for example hydrohalic, e.g. hydrochloric or hydrobromic acid; sulfuric, phosphoric or nitric acid; aliphatic or aromatic sulfonic acids, e.g. methanesulfonic acid, ethanesulfonic acid, hydroxyethanesulfonic, benzenesulfonic, p-toluenesulfonic or naphthalenesulfonic, aliphatic or aromatic carboxylic acids e.g. acetic, propionic, succinic, glycollic, lactic, malic, tartaric, gluconic, citric, maleic, fumaric, pyruvic, phenylacetic, benzoic, 4-aminobenzoic, anthranilic, 4-hydroxybenzoic, salicylic, 4-aminosalicylic, pamoic, nicotinic acid; or ascorbic acid.

The compounds of the invention exhibit valuable pharmacological properties, e.g. gastrointestinal antisecretory effects, particularly anti-diarrheal effects, by inter alia inhibiting calmodulin activity in mammals.

Said effects are demonstrable by in vitro and in vivo tests, using advantageously mammals, e.g. mice, rats, or dogs, as test subjects. Said compounds can be applied to them enterally or parenterally, advantageously orally, subcutaneously, intravenously or intraperitoneally, for example, within gelatin capsules or in the form of aqueous solutions or suspensions respectively. The applied dosage may range between about 0.10 and 100 mg/kg/day, preferably between about 0.50 and 50 mg/kg/day, advantageously between about 5 and 30 mg/kg/day. The applied dosage in vitro may range between about $10^{-4}$ and $10^{-8}$M concentration, preferably between about $10^{-5}$ and $10^{-7}$M.

The calmodulin inhibitory properties indicative of the antisecretory activity of said new compounds are determined in vitro by measuring the inhibition of the calmodulin induced activation of bovine c-AMP phosphodiesterase, according to the method described by J. A. Norman et al, Mol. Pharmacology 16, 1089 (1979).

Illustrative of the invention, 1,3-dihydro-1-{1-[(4-methyl-4H,6H-pyrrolo[1,2-a][4,1]benzoxazepin-4-yl]methyl]-4-piperidinyl}-2H-benzimidazol-2-one maleate inhibits calmodulin-induced activation of phosphodiesterase in vitro by 50% at a concentration of about $3 \times 10^{-6}$ Molar.

The antidiarrheal effect of the compounds of the invention is determined by measuring the inhibition of the diarrhea induced in rats by the intraperitoneal administration of prostaglandin $E_2$.

The test is carried out as follows:

Female Sprague-Dawley rats weighing 200–250 g and fasted for 18 hours are employed. The test compounds are dissolved in dimethylsulfoxide diluted with water to a 30–50% dimethyl sulfoxide concentration and administered orally by gastric lavage in a volume of 1 ml/Kg. Thirty or sixty minutes later, prostaglandin $E_2$ (150 μg) is administered i.p. in a volume of 0.5 ml of water. The decrease in fecal excretion compared to untreated animals is measured for a period of 30 minutes after administration of prostaglandin $E_2$.

Illustrative of the invention, 1,3-dihydro-1-{1-[(4-methyl-4H,6H-pyrrolo[1,2-a][4,1]benzoxazepin-4-yl)methyl]-4-piperidinyl}-2H-benzimidazol-2-one maleate reduces prostaglandin $E_2$ induced fecal excretion at a dose of 10 mg/Kg p.o. in the rat.

Inhibition of acid secretion, indicative of antiulcer activity, can be determined in vitro in rat stomach parietal cells as follows:

Approximately $1 \times 10^6$ parietal cells (18–22% enriched) are incubated in a balanced salt solution containing glucose, BSA (bovine serum albumin), 0.1 uCi of $^{14}$C-aminopyrine, histamine (1 mM), isobutyl methylxanthine (0.1 mM) and the compound to be tested under 95% oxygen at 37° C. for a period of 40 minutes. The cells are then washed, ruptured with distilled water and analyzed by scintillation spectrometry. A decrease in the accumulation of $^{14}$C-aminopyrine in the cells represents an indirect measure of the inhibition of acid secretion.

Illustrative of the invention, 1,3-dihydro-1-{1-[(4-methyl-4H,6H-pyrrolo[1,2-a][4,1]-benzoxazepin-4-yl]-4-piperidinyl}-2H-benzimidazol-2-one maleate inhibits acid secretion in rat stomach parietal cells, showing an $IC_{50}$ of about $3 \times 10^{-7}$M.

Accordingly, the compounds of the invention are useful as gastrointestinal medicinal agents, e.g. as gastrointestinal antisecretory agents, for example for the treatment or management of diarrhea, ulcers, excess gastric acidity, inflammatory bowel disease and dehydration.

The compounds of the invention, i.e. the compounds of formula I or II, and salts thereof, are advantageously prepared according to the following processes:

(a) condensing an amine corresponding to the group $R_4$ in formula I, namely a compound of the formula $$R_4\text{-H} \qquad (III)$$

wherein $R_4$ has meaning as defined above and H is attached to the amino nitrogen of said group $R_4$; with a compound of the formula

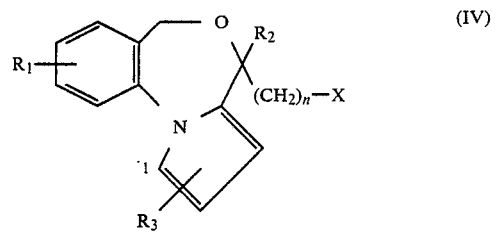

(IV)

wherein n, $R_1$, $R_2$ and $R_3$ have meaning as defined above for compounds of formula I and X represents reactive esterified hydroxy; or with a compound of the formula

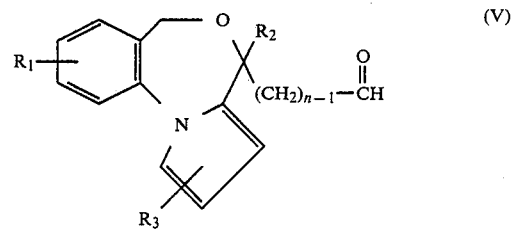

(V)

wherein n, $R_1$, $R_2$ and $R_3$ have meaning as defined above for compounds of formula I under conditions of reductive amination;

(b) reducing a compound of the formula

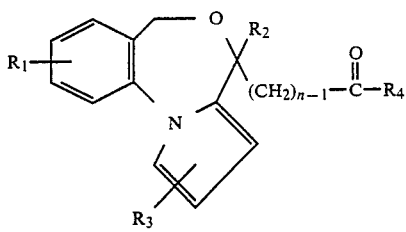

(VI)

wherein n and $R_1$ to $R_4$ have meaning as defined above for compounds of formula I; and carrying out the said processes while, if necessary, temporarily protecting any interfering reactive group(s) in all these processes, and then isolating the resulting compound of the formula I and, if desired, converting a resulting compound of formula I into another compound of the invention, and/or, if desired, converting a resulting free compound into a salt or a resulting salt into the free compound or into another salt, and/or, if desired, separating a mixture of isomers or racemates obtained into the single isomers or racemates, and/or, if desired, resolving a racemate obtained into the optical antipodes.

A reactive esterified hydroxy group in the above mentioned processes is hydroxy esterified by a strong acid, especially a strong inorganic acid, such as a hydrohalic acid, especially hydrochloric, hydrobromic or hydriodic acid, or sulphuric acid, or by a strong organic acid, especially a strong organic sulfonic acid, such as an aliphatic or aromatic sulfonic acid, for example methanesulfonic acid, 4-methylphenylsulfonic acid or 4-bromophenylsulfonic acid. Said reactive esterified hydroxy group is especially halo, for example chloro, bromo or iodo, or aliphatically or aromatically substituted sulfonyloxy, for example phenylsulfonyloxy or 4-methylphenylsulfonyloxy (tosyloxy).

In starting compounds and intermediates which are converted to the compounds of the invention in a manner described herein, functional groups present, such as formyl, carboxy, amino and hydroxy groups, are optionally protected by conventional protecting groups that are common in preparative organic chemistry. Protected formyl, carboxy, amino and hydroxy groups are those that can be converted under mild conditions into free formyl, carboxy, amino and hydroxy groups without the molecular framework being destroyed or other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (carbonyl group, carboxy group, amino group etc.), the structure and stability of the molecule of which the substituent is a part, and the reaction conditions.

Well-known protecting groups that meet these conditions and their introduction and removal are described, for example, in J. F. W. McOmie, "Protective Groups in Organic Chemistry", Plenum Press, London, N.Y. 1973, T. W. Greene, "Protective Groups in Organic Synthesis", Wiley, N.Y. 1981, and also in "The Peptides", Vol. I, Schroeder and Luebke, Academic Press, London, N.Y. 1965, as well as in Houben-Weyl, "Methoden Der Organischen Chemie", Vol. 15/1, George Thieme Verlag, Stuttgart, 1974.

The preparation of compounds of the invention according to process (a) involving the N-alkylation of an amine of formula III with a compound of formula IV is carried out in a conventional manner, usually in the presence of a inert solvent or mixture of inert solvents, and, if necessary, with cooling or heating, for example at a temperature range of from approximately −20° C. to approximately 150° C., and/or in an inert gas atmosphere. The reaction is carried out advantageously in the presence of a base, such as an inorganic base, for example an alkali metal or alkaline earth metal carbonate, hydride or hydroxide, or in the presence of an organic base, such as an alkali metal lower alkoxide, or a tertiary amine such as triethylamine or pyridine.

The preparation of compounds of the invention according to process (a) involving the condensation of an amine of formula III with an aldehyde of formula V by reductive N-alkylation is carried out under conditions known to the art, e.g. by catalytic hydrogenation with hydrogen in the presence of platinum, palladium or nickel catalysts or with chemical reducing agents such as simple or complex light metal hydrides, advantageously an alkali metal cyanoborohydride such as sodium cyanoborohydride. The reductive amination with an alkali metal cyanoborohydride is preferably carried out in an inert solvent, e.g. methanol or acetonitrile, advantageously in the presence of an acid, e.g. hydrochloric acid or acetic acid.

Process (a) is preferred for the preparation of the compounds of formula I wherein an amide functional grouping is present in the final product.

The preparation of the compounds of the invention according to process (b) is preferably carried out by reduction with a simple or complex hydride reducing agent known in the art for reduction of an amide function e.g. lithium aluminum hydride or borane in an inert solvent, such as tetahydrofuran or diethyl ether, advantageously at a temperature ranging from room temperature to a temperature near the boiling point of the solvent.

The starting amines of formula III are known, or if not known are prepared by methods well-known in the art.

The starting materials of formula IV and V are prepared using functional group transformations well-known in the art.

An ester of the appropriately substituted anthranilic acid is condensed with a 2,5-di-lower alkoxytetrahydrofuran e.g. with heat in acetic acid, to obtain the o-(1-pyrrolyl)-benzoic acid ester, e.g. a lower alkyl ester, which is subsequently reduced, e.g. with lithium aluminum hydride in an inert solvent to the appropriately substituted o-(1-pyrrolyl)-benzyl alcohol of formula VII.

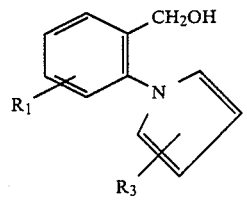

(VII)

wherein $R_1$ and $R_3$ have meaning as defined for the compounds of formula I.

Condensation of a compound of formula VII with a compound of the formula VIII

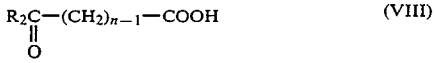

wherein n and $R_2$ have meaning as defined above, or an ester thereof, e.g. a lower alkyl ester, advantageously in the presence of a strong base, e.g. butyl lithium or lithium diisopropylamide, or in the presence of an acid, e.g. hydrobromic acid, yields a compound of the formula IX

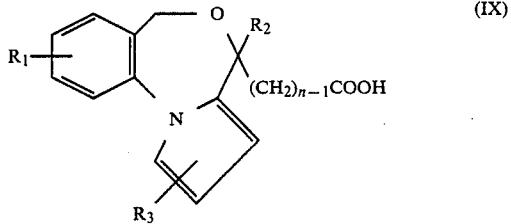

or an ester thereof, e.g. a lower alkyl ester wherein n, $R_1$, $R_2$ and $R_3$ have meaning as defined above for the compounds of formula I.

Reduction of an ester of a compound of formula IX with a selective chemical reducing agent, e.g. diisobutyl aluminum hydride, yields the aldehyde intermediate of formula V.

Reduction of a compound of formula IX with a reducing agent, known to be effective for the reduction of a carboxylic acid or ester to the corresponding alcohol, e.g. diborane, sodium bis-(2-methoxyethoxy)-aluminum hydride) or lithium aluminum hydride yields a compound of the formula IV wherein X represents hydroxy.

Said compounds of formula IV wherein X represents hydroxy are converted to the corresponding compounds of formula IV wherein X represents esterified hydroxy as defined above using procedures well-known in the art. For example conversion to the compounds of formula IV wherein X represents halo such as chloro or bromo is carried with conventional reagents such as thionyl chloride or phosphorus oxychloride.

The starting materials of formula VI are prepared by condensation of a carboxylic acid of formula IX or a reactive functional derivative thereof with an amine corresponding to the group $R_4$ in formula I, namely a compound of the formula $R_4$-H wherein $R_4$ has meaning as defined above and H is attached to the amino nitrogen of said group $R_4$, under conditions known in the art for the formation of an amide bond.

A reactive functional derivative of a carboxylic acid of formula IX above represents e.g. an acyl halide such as the acid chloride, the anhydride of said acid, a mixed anhydride e.g. such derived from a lower alkyl halocarbonate such as ethyl chloroformate, a reactive ester, e.g. a lower alkyl ester such as an ethyl or methyl ester or an optionally substituted phenyl ester, or an amide, e.g. such derived from imidazole (prepared from N,N-carbonyldiimidazole).

The condensation of an amine of formula III ($R_4$-H) in suitably protected form depending on nature of substituents, with a compound of formula IX in the form of the free carboxylic acid is carried out advantageously in the presence of a condensing agent such as dicyclohexylcarbodiimide or 1,1'-diimidazolylcarbonyl (carbonyldiimidazole) in an inert solvent, such as methylene chloride or tetrahydrofuran, at a temperature near the boiling point of the solvent.

The condensation of a compound of formula III with a reactive functional derivative of an acid of formula IX in the form of e.g. an acid halide, advantageously an acid chloride, or mixed anhydride, is carried out in an inert solvent such as toluene or methylene chloride, advantageously in the presence of a base, e.g. an inorganic base such as potassium carbonate or an organic base such as triethylamine or pyridine, at a temperature ranging from about 0° to 100°, preferably at room temperature.

The compounds of the invention obtained by the above-cited processes can be converted into other compounds of the invention of formula I according to methodology known in the art.

For example, the conversion of the compounds of formula I wherein $R_1$ represents lower alkoxy to the compounds of formula I wherein $R_1$ represents hydroxy is carried out by methods well-known in the art, e.g., with a mineral acid, such as hydriodic acid or, advantageously for compounds wherein lower alkoxy is methoxy, with e.g. boron tribromide in methylene chloride or with sodium or lithium diphenylphosphide in tetrahydrofuran.

The above-mentioned reactions are carried out according to standard methods, in the presence or absence of diluents, preferably such as are inert to the reagents and are solvents thereof, of catalysts, condensing or said other agents respectively and/or inert atmosphere, at low temperatures, room temperature or elevated temperatures preferably near the boiling point for the solvents used, at atmospheric or superatmospheric pressure.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts. Whenever desirable, the above processes are carried out after first suitably protecting and potentially interfering reactive functional groups, as illustrated above or in the examples herein.

Advantageously, those starting materials should be used in said reactions, that lead to the formation of those compounds indicated above as being preferred.

Finally, the compounds of the invention are either obtained in the free form, or as a salt thereof. Any resulting base can be converted into a corresponding acid addition salt, preferably with the use of a pharmaceutically acceptable acid or anion exchange preparation, or resulting salts can be converted into the corresponding free bases, for example, with the use of a stronger base, such as a metal or ammonium hydroxide, or any basic salt, e.g., an alkali metal hydroxide or carbonate, or a cation exchange preparation. These or other salts, for example, the picrates, can also be used for purification of the basis obtained. In view of the close relationship between the free compounds and the compounds in the form of their salts, whenever a compound is referred to in this context, a corresponding salt is also intended, provided such is possible or appropriate under the circumstances.

The compounds, including their salts, may also be obtained in the form of their hydrates, or include other solvents used for the crystallization.

The present invention additionally relates to the use in mammals of the compounds of formula I and their pharmaceutically acceptable, non-toxic acid addition salts, or pharmaceutical compositions thereof, as medicaments, especially as gastrointestinal agents, particularly as gastrointestinal antisecretory agents for the treatment of gastrointestinal secretory disorders, comprising diarrhea, ulcers, inflammatory bowel disease and dehydration.

The present invention also relates to the use of the compounds of the invention for the preparation of pharmaceutical compositions, especially gastrointestinal antisecretory pharmaceutical compositions, and more particularly antidiarrheal pharmaceutical compositions having calmodulin inhibitory activity.

The pharmaceutical compositions according to the invention are those suitable for enteral, such as oral or rectal, transdermal and parenteral administration to mammals, including man, comprising an effective amount of a pharmacologically active compound of formula I or a pharmaceutically acceptable salt thereof, alone or in combination with one or more pharmaceutically acceptable carriers.

The pharmacologically active compounds of the invention are useful in the manufacture of pharmaceutical compositions comprising an effective amount thereof in conjunction or admixture with with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid or its magnesium or calcium salts, and/or polyethyleneglycol; for tablets also (c) binders, e.g. magnesium aluminum silicate, starch paste, gelatin, tragacanth, methylcellulose, sodium carboxymethylcellulose and/or polyvinylpyrrolidone; if desired, (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositons may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of formula I with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

More specifically, the invention also relates advantageously to the method of treatment of disorders in mammals responsive to calmodulin inhibition, particularly gastrointestinal secretory disorders such as secretory diarrhea, ulcers, inflammatory bowel disease and dehydration, using an effective amount of a compound of the invention (of formula I or a pharmaceutically acceptable salt thereof), preferably in the form of above-cited pharmaceutical compositions. The dosage of active compound administered is dependent on the species of warm-blooded animal (mannal), the body weight, age and individual condition, and on the form of administration.

A unit dosage for a mammal of about 50 to 70 kg may contain between about 5 and 100 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. The structure of final products, intermediates and starting materials is confirmed by analytical methods, e.g. microanalysis and spectroscopic characteristics (e.g. IR, NMR).

EXAMPLE 1

1,3-Dihydro-1-{1-[(4-methyl-4H,6H,-pyrrolo[1,2-a][4,1]-benzoxazepin-4-yl)-methyl]-4-piperidinyl}-2H-benzimidazol-2-one (1:1)maleate To a suspension of 3.0 g of 1,3-dihydro-1-{1-[(4-methyl-4H,6H-pyrrolo[1,2-a][4,1]benzoxazepin-4-yl)carbonyl]-4-piperidinyl}-2H-benzimidazol-2-one in 120 ml of tetrahydrofuran is added 700 mg of lithium aluminum hydride. The reaction mixture is then heated at reflux temperature for 6 hours followed by stirring at room temperature for 18 hours. The reaction mixture is diluted with 150 ml of ether and the excess lithium aluminum hydride destroyed in the usual manner described below. The resulting granular precipitate is removed by filtration. The organic phase is washed with 150 ml of dilute sodium hydroxide and then 150 ml of brine. The organic extracts are then dried over magnesium sulfate, filtered and solvent evaporated under reduced pressure to yield 1,3-dihydro-1-{1-[(4-methyl-4H,6H-pyrrolo[1,2-a][4,1]-benzoxazepin-4-yl)-methyl]-4-piperidinyl}-2H-benzimidazol-2-one, m.p. 199°–201°, the compound of formula II wherein $R_1$ and $R_5$=H, and $R_2$=$CH_3$ and n=1.

This is then converted into its maleate salt by dissolving separately the free base and a molar equivalent amount of maleic acid in acetone, and combining the solutions. The 1:1 maleate salt crystallizes upon standing, has m.p. 183°–185°.

The 1:1 fumarate salt prepared in a similar manner has a melting point of 125°–127°.

The starting material is prepared as follows:

A mixture of 500 g of methyl anthranilate and 438 g of 2,5-dimethoxytetrahydrofuran in 670 ml of glacial acetic acid is heated at reflux temperature for 1½ hours. The acetic acid is then evaporated under reduced pressure and the residue is distilled to yield methyl 2-(1H-pyrrol-1-yl)-benzoate, b.p. 109°/0.1 mm Hg.

To a suspension of 117 g of lithium aluminum hydride in 2 L of anhydous ether (under an inert atmosphere) is added dropwise a solution of 428 g of methyl 2-(pyrrol-1-yl)-benzoate in 1.5 L of ether over a period of 4 hours. The reaction mixture is then heated at reflux temperature for an additional 4 hours and then allowed to cool to room temperature. After cooling in an ice-bath, the excess lithium aluminum hydride is destroyed by the dropwise addition of 117 ml of water over 1 hour, followed by dropwise addition of 117 ml of 15% sodium hydroxide and subsequent addition of 351 ml of water over a 30 minute period. The resultant granular solid is separated by filtration, the ether layer is then dried over magnesium sulfate and the solvent evaporated under reduced pressure to yield 2-(pyrrol-1-yl)-benzyl alcohol which may be further purified by distillation in vacuo; b.p. 110°–114°/0.1 mm Hg.

To a solution of 34.6 g of 2-(pyrrol-1-yl)-benzyl alcohol in 300 ml of anhydrous tetrahydrofuran and 32 ml of tetramethylethylene diamine (TMEDA) is added 183 ml of a 2.4 molar solution of n-butyl lithium in such a manner that the internal temperature of the reaction is maintained below 30°. On completion of the addition, the reaction mixture is stirred at room temperature for 3 hours. The reaction mixture is then cooled to $-70°$ by means of a dry-ice/acetone bath, and 24 ml of ethyl pyruvate is added to the mixture over 1 minute. The reaction is then allowed to warm to room temperature and stirred overnight (18 hours). The reaction is then poured into an ice-water/ether mixture and the organic phase separated, dried over magnesium sulfate and the solvent evaporated under reduced pressure to yeild ethyl 4-methyl-4H,6H-pyrrolo[1,2-a][4,1]benzoxazepine-4-carboxylate, m.p. 94°–96°, which may be recrystallized from a mixture of ether-hexane (1:1).

The mixture of 41 g thereof, 180 ml of 3N sodium hydroxide and 150 ml of ethanol is heated at reflux temperature for 6 hours. The ethanol is then removed by evaporation under reduced pressure and the aqueous solution is acidified to pH 5 with 6N HCl. The resulting product, 4-methyl-4H,6H-pyrrolo[1,2-a][4,1]benzoxazepine-4-carboxylic acid, m.p. 182°–183°, is collected by filtration, and may be recrystallized from aqueous ethanol.

To a solution of 7.5 g thereof, in 300 ml of tetrahydrofuran is added 5 g of 1,1'-carbonyldiimidazole and the resultant mixture stirred at room temperature for 1 hour. To this mixture is added 5 g of 1,3-dihydro-1-(4-piperidyl)-2H-benzimidazol-2-one, and the reaction is heated at reflux temperature for 48 hours. After cooling to room temperature, the reaction mixture is poured into 150 ml of ice-water and extracted into 150 ml of methylene chloride. The organic extracts are washed successively with 150 ml of sodium carbonate solution, 150 ml of water and 150 ml of dilute hydrochloric acid, then dried over magnesium sulfate, filtered, and the solvent is evaporated under reduced pressure to yield 1,3-dihydro-1-{1-[(4-methyl-4H,6H-pyrrolo[1,2-a][4,1]benzoxazepin-4-yl)carbonyl]-4-piperidinyl}-2H-benzimidazol-2-one, m.p. 208°–210°.

EXAMPLE 2

1,3,4,5-Tetrahydro-1-{1-[(4-methyl-4H,6H-pyrrolo[1,2-a][4,1]benzoxazepin-4-yl)methyl]-4-piperidinyl}-2H-imidazol-2-one To a solution of 4.5 g of 4-formyl-4-methyl-4H,6H-pyrrolo[1,2-a][4,1]benzoxazepine in 50 ml of methanol is added 3.6 ml of 5.5N methanolic HCl and 3.4 g of 1,3,4,5-tetrahydro-1-(4-piperidinyl)-2H-imidazol-2-one followed by 900 mg of sodium cyanoborohydride. The reaction mixture is allowed to stir at room temperature for 8 days. 2 ml of conc. HCl is added to the reaction mixture and the solvent is removed by evaporation under reduced pressure. The residue is dissolved in 150 ml water and washed with 150 ml of 1:1 ethyl acetate-ether mixture. The aqueous phase is separated, basified with dilute sodium hydroxide to pH 9 and extracted with 2×150 ml of ethyl acetate. The combined ethyl acetate extracts are dried over anhydrous $MgSO_4$, filtered, and the solvent is removed by evaporation under reduced pressure to yield 1,3,4,5-tetrahydro-1-{1-[(4-methyl-4H,6H-pyrrolo[1,2-a][4,1]benzoxazepin-4-yl)-methyl]-4-piperidinyl}-2H-imidazol-2-one which is characterized as its maleate salt, m.p. 197°–199°.

The starting material is prepared as follows:

A solution of 7.0 g of ethyl 4-methyl-4H,6H-pyrrolo[1,2-a][4,1]benzoxazepine-4-carboxylate (for preparation see Example 1) in 200 ml of methylene chloride is cooled to $-65°$ and 65 ml of 1.0 m diisobutylaluminum hydride in methylene chloride is added dropwise over a 30 minute period. On completion of the addition, the reaction is stirred for 30 minutes at $-60°$ followed by quenching of the reaction with methanol. Water is then added and the cooling bath is removed. The reaction mixture is allowed to reach room temperature and stirred for 15 minutes. Solids are removed by filtration and the methylene chloride solution is dried over anhydrous $MgSO_4$ and the solvent evaporated under reduced pressure to yield an oily residue which on crystallization ether yields 4-formyl-4-methyl-4H,6H-pyrrolo[1,2-a][4-1]benzoxazepine, m.p. 83°–85°.

EXAMPLE 3

Prepared essentially according to procedures described in the previous examples are:

(a) 8-[(4-methyl-4H,6H-pyrrolo[1,2-a][4,1]benzoxazepin-4-yl)-methyl]-1-phenyl-1,3,8-triazaspiro[4,5]decan-4-one.

(b) 1-[(4-methyl-4H,6H-pyrrolo[1,2-a][4,1]benzoxazepin-4-yl)-methyl]-4-hydroxy-4-phenylpiperidine 1:1 maleate, m.p. 175–177.

(c) 1-[(4-methyl-4H,6H-pyrrolo[1,2-a][4,1]benzoxazepin-4-yl)-methyl]-4-hydroxy-4-(p-chlorophenyl)-piperidine.

(d) 1-[(4-methyl-4H,6H-pyrrolo[1,2-a][4,1]benzoxazepin-4-yl)-methyl]-4-phenylpiperazine dihydrochloride, m.p. 155°–157°.

(e) 1-[4-methyl-4H,6H-pyrrolo[1,2-a][4,1]benzoxazepin-4-yl)-methyl]-4-phenylpiperidine 1:1 maleate, m.p. 129°–131°.

(f) 1-[(4-methyl-4H,6H-pyrrolo[1,2-a][4,1]benzoxazepin-4-yl)-methyl]-4-methylpiperazine 1:1 maleate, m.p. 128°–30°.

(g) 1,3-dihydro-1-{1-[(8-chloro-4-methyl-4H,6H-pyrrolo[1,2-a][4,1]benzoxazepin-4-yl)-methyl]-4-piperindinyl}-2H-benzimidazol-2-one.

EXAMPLE 4

(A) Preparation of 10,000 tablets each containing 10 mg of the active ingredient:

Formula:

| 1,3-dihydro-1- 1-[{(4-methyl-4H,6H-pyrrolo[1,2-a][4,1]-benzoxazepin-4-yl)-methyl]-4-piperidinyl}-2H-benzimidazol-2-one 1:1 maleate | |
|---|---|
| | 100.00 g |
| lactose | 2,400.00 g |
| Corn starch | 125.00 g |
| Polyethylene glycol 6,000 | 150.00 g |

-continued

| 1,3-dihydro-1- 1-[{(4-methyl-4H,6H-pyrrolo[1,2-a][4,1]-benzoxazepin-4-yl)-methyl]-4-piperidinyl}-2H-benzimidazol-2-one 1:1 maleate | |
|---|---|
| Magnesium stearate | 40.00 g |
| Purified water | q.s. |

Procedure:

All the powders are passed through a screen with openings of 0.6 mm. Then the drug substance, lactose, magnesium stearate and half of the starch are mixed in a suitable mixer. The other half of the starch is suspended in 65 ml of water and the suspension added to the boiling solution of the polyethylene glycol in 260 ml of water. The paste formed is added to the powders, which are granulated, if necessary, with an additional amount of water. The granulate is dried overnight at 35°, broken on a screen with 1.2 mm openings and compressed into tablets, using concave punches uppers bisected.

(B) Preparation of 1,000 capsules each containing 10 mg of the active ingredient:

Formula:

| 1,3-dihydro-1-{1-[(4-methyl-4H,6H-pyrrolo[1,2-a][4,1]-benzoxazepin-4-yl)-methyl]-4-piperidinyl}-2H-benzimidazol-2-one 1:1 maleate | |
|---|---|
|  | 10.0 g |
| Lactose | 207.0 g |
| Modified starch | 80.0 g |
| Magnesium stearate | 3.0 g |

Procedure:

All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 300 mg of said mixture each, using a capsule filling machine.

Analogously tablets and capsules are prepared, containing about 5-100 mg of the other compounds disclosed and exemplified herein.

What is claimed is:

1. A compound of the formula

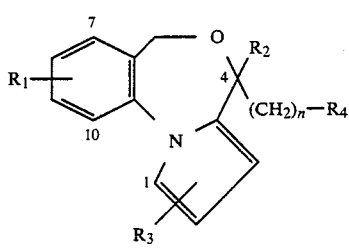

(I)

wherein n represents the integer 1, 2, 3 or 4; $R_1$ represents hydrogen, lower alkyl, halogen, trifluoromethyl, hydroxy or lower alkoxy; $R_2$ represents hydrogen or lower alkyl; $R_3$ represents hydrogen, lower alkyl or halogen; $R_4$ represents amino, lower alkylamino, di-lower alkylamino, morpholino, N-lower alkyl or N-aryl-piperazino in which aryl represents phenyl or phenyl monosubstituted by lower alkyl or halogen, pyrrolidino, piperidino or substituted piperidino selected from

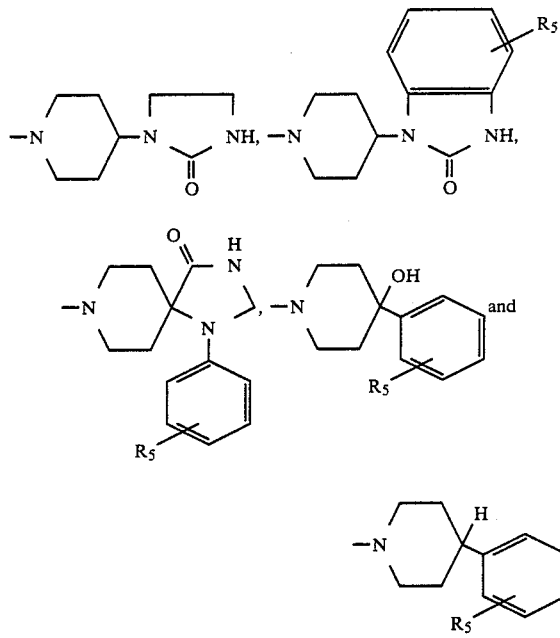

in which $R_5$ represents hydrogen, halogen or lower alkyl; or a pharmaceutically acceptable salt thereof.

2. A compound according to claim 1 of formula I wherein n represents 1 or 2; $R_4$ represents substituted piperidino as defined in claim 1; or a pharmaceutically acceptable salt thereof.

3. A compound according to claim 1 of the formula

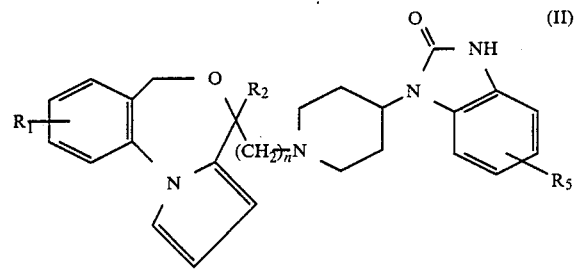

(II)

wherein $R_1$ represents hydrogen, lower alkyl, halogen, trifluoromethyl, hydroxy or lower alkoxy; $R_2$ represents hydrogen or lower alkyl; n represents an integer from 1 to 4; and $R_5$ represents hydrogen, halogen or lower alkyl; or a pharmaceutically acceptable salt thereof.

4. A compound according to claim 3 of formula II wherein n represents the integer 1 or 2; $R_2$ represents straight chain lower alkyl of 1 to 4 carbon atoms; $R_1$ and $R_5$ represent hydrogen or halogen; or a pharmaceutically acceptable salt thereof.

5. A compound according to claim 3 of formula II wherein $R_1$ and $R_5$ represent hydrogen; $R_2$ represents methyl; and n represents the integer 1; or a pharmaceutically acceptable salt thereof.

6. A gastrointestinal antisecretory pharmaceutical composition suitable for administration to a mammal comprising an effective antisecretory amount of a compound of claim 1 in combination with one or more pharmaceutically acceptable carriers.

7. An antidiarrheal pharmaceutical composition suitable for administration to a mammal comprising an effective antidiarrheal amount of a compound of claim 5 in combination with one or more pharmaceutically acceptable carriers.

8. A method of treating calmodulin mediated diarrhea in a mammal which comprises administering to a mammal in need thereof an effective antidiarrheal amount of a compound of claim 3 or an effective antidiarrheal amount of a pharmaceutical composition comprising a compound of claim 3 in combination with one or more pharmaceutically acceptable carriers.

9. A method of treating calmodulin mediated diarrhea in a mammal which comprises administering to a mammal in need thereof an effective antidiarrheal amount of a compound of claim 4 or an effective antidiarrheal amount of a pharmaceutical composition comprising a compound of claim 4 in combination with one or more pharmaceutically acceptable carriers.

10. A method of treating calmodulin mediated diarrhea in a mammal which comprises administering to a mammal in need thereof an effective antidiarrheal amount of a compound of claim 5 or an effective antidiarrheal amount of a pharmaceutical composition comprising a compound of claim 5 in combination with one or more pharmaceutically acceptable carriers.

11. A method of inhibiting gastric acid secretion in a mammal which comprises administering to a mammal in need thereof an effective gastric acid secretion inhibiting amount of a compound of claim 3 or an effective gastric acid secretion inhibiting amount of a pharmaceutical composition comprising a compound of claim 3 in combination with one or more pharmaceutically acceptable carriers.

12. A method of treating calmodulin mediated gastrointestinal secretory disorders in a mammal which comprises administering to a mammal in need thereof an effective gastrointestinal secretion inhibiting amount of a compound of claim 3 or an effective amount of a pharmaceutical composition comprising a compound of claim 3 in combination with one or more pharmaceutically acceptable carriers.

13. A method of inhibiting calmodulin activity in a mammal which comprises administering to a mammal in need thereof an effective calmodulin inhibiting amount of a compound of claim 1 or an effective calmodulin inhibiting amount of a pharmaceutical composition comprising a compound of claim 1 in combination with one or more pharmaceutically acceptable carriers.

14. A compound of the formula

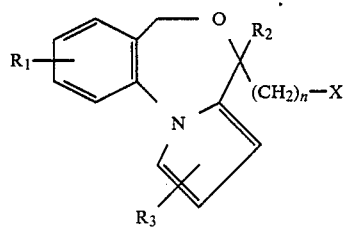

(IV)

wherein n represents the integer 1, 2, 3 or 4; $R_1$ represents hydrogen, lower alkyl, halogen, trifluoromethyl, hydroxy or lower alkoxy; $R_2$ represents hydrogen or lower alkyl; $R_3$ represents hydrogen, lower alkyl or halogen; and X represents hydroxy; or a compound of the formula

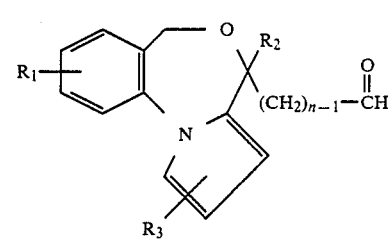

(V)

wherein n, $R_1$, $R_2$ and $R_3$ have meaning as defined above; or a compound of the formula

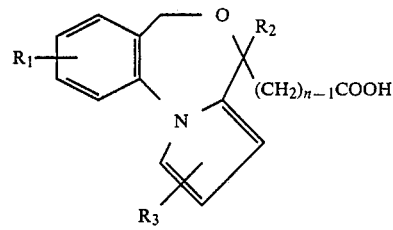

(IX)

or a reactive ester selected from lower alkyl or phenyl ester wherein n, $R_1$, $R_2$ and $R_3$ have the meaning as defined above.

15. A compound of the formula

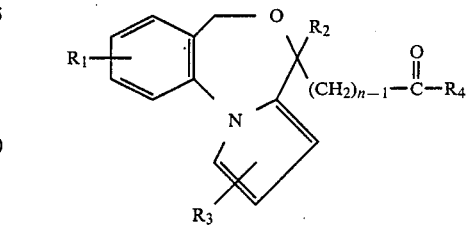

(VI)

wherein n represents the integer 1, 2, 3 or 4; $R_1$ represents hydrogen, lower alkyl, halogen, trifluoromethyl, hydroxy or lower alkoxy; $R_2$ represents hydrogen or lower alkyl; $R_3$ represents hydrogen, lower alkyl or halogen; $R_4$ represents amino, lower alkylamino, di-lower alkylamino, morpholino, N-lower alkyl or N-aryl-piperazino in which aryl represents phenyl or phenyl monosubstituted by lower alkyl or halogen, pyrrolidino, piperidino or substituted piperidino selected from

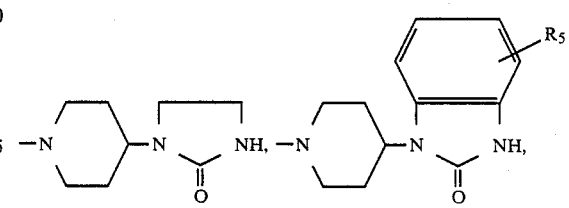

-continued
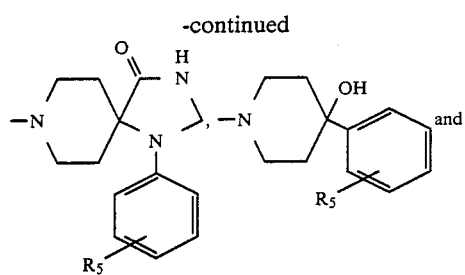
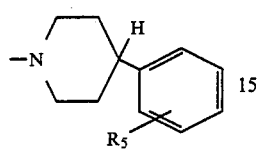
in which $R_5$ represents hydrogen, halogen or lower alkyl.
* * * * *